United States Patent [19]

Smith, Jr.

[11] Patent Number: 4,477,457

[45] Date of Patent: Oct. 16, 1984

[54] METHOD FOR INDUCING ANOREXIA USING NALMETRENE

[75] Inventor: Dewey H. Smith, Jr., Wilmington, Del.

[73] Assignee: E. I. Du Pont de Nemours and Company, Wilmington, Del.

[21] Appl. No.: 437,324

[22] Filed: Oct. 28, 1982

[51] Int. Cl.³ .............................................. A61K 31/485
[52] U.S. Cl. .................................................... 424/260
[58] Field of Search ........................................ 424/260

[56] References Cited

U.S. PATENT DOCUMENTS

| | | | |
|---|---|---|---|
| 3,393,197 | 7/1968 | Pachter et al. | 260/285 |
| 3,814,768 | 6/1974 | Fishman | 260/285 |
| 3,896,226 | 7/1975 | Fishman | 424/260 |
| 4,217,353 | 8/1980 | Smith | 424/260 |
| 4,322,426 | 3/1982 | Hermann et al. | 424/260 |
| 4,366,159 | 12/1982 | Magruder | 424/260 |

OTHER PUBLICATIONS

Miller, *Am J. Hosp. Pharm.*, 37, 942–949 (1980).
Holtzman, *J. Pharmacol. Exp. Ther.*, 189, 51–60 (1974).
Holtzman, *Life Sciences*, 16, 1465–1470 (1975).

*Primary Examiner*—Douglas W. Robinson

[57] ABSTRACT

Nalbuphine or nalmetrene can be administered orally so as to effect appetite suppression in mammals.

4 Claims, No Drawings

METHOD FOR INDUCING ANOREXIA USING NALMETRENE

BACKGROUND OF THE INVENTION

This invention relates to inducing anorexia in warm-blooded animals by administering nalbuphine or nalmetrene orally thereto.

Nalbuphine, otherwise known as 17-cyclobutylmethyl-4,5α-epoxymorphinan-3,6α,14-triol, is known to possess both analgesic and narcotic antagonist activity. The compound and methods for preparing it are described in Pachter et al., U.S. Pat. No. 3,393,197, the disclosure of which is hereby incorporated by reference. The pharmacology of nalbuphine is reviewed by Miller, *Am. J. Hosp. Pharm.*, 37, 942–9 (1980).

Nalmetrene is the common name for the compound 17-cyclopropylmethyl-4,5α-epoxy-6-methylenemorphinan-3,14-diol. This compound is known to be a potent narcotic antagonist and is disclosed in Fishman, U.S. Pat. Nos. 3,814,768 and 3,896,226, the disclosures of which are hereby incorporated by reference.

Smith, U.S. Pat. No. 4,217,353, which issued on Aug. 12, 1980, discloses that another narcotic antagonist, naltrexone ((−)-17-cyclopropylmethyl-4,5α-epoxy-3,14-dihydroxymorphinan-6-one), can be administered orally to effect appetite suppression in mammals. Holtzman, *J. Pharmacol. Exp. Ther.*, 189, 51–60 (1974), has shown that the narcotic antagonist naloxone (N-allyl-14-hydroxy-7,8-dihydronormorphinone) suppresses eating by food-deprived rats but not by food-deprived mice. In a subsequent study, Holtzman showed that the fluid intake (sweetened Enfamil) of rats was reduced following subcutaneous administration of naloxone, naltrexone or nalorphine (N-allylnormorphine); *Life Sciences*, 16, 1465–70 (1975).

There is no indication in the known art that either nalbuphine or nalmetrene would be an effective appetite suppressant. In addition, the art does not disclose anorexigenic activity for any mixed agonist/antagonists such as nalbuphine.

SUMMARY OF THE INVENTION

A method for exerting an anorexigenic effect in mammals has now been discovered. This method comprises orally administering to a mammal an effective anorexigenic dose of nalbuphine, nalmetrene, or pharmaceutically suitable salts of either. These compounds are neither stimulants nor depressants, and they do not cause central nervous system excitement, sedation, hypothermia or other side effects. They therefore avoid many of the disadvantages connected with other appetite supressants currently available.

DETAILED DESCRIPTION

The preparation of nalbuphine and nalmetrene are disclosed in U.S. Pat. Nos. 3,393,197 and 3,814,768, respectively, which have been cited previously. Pharmaceutically suitable salts of these compounds are known and include hydrochloride, hydrobromide, neutral and acid sulfate, phosphates, nitrate, acetate, benzoate, salicyclic, neutral and acid fumarate and maleate, terephthalate, ethanesulfonate, bitartrate and others.

The anorexigenic activities of nalbuphine and nalmetrene are demonstrated by administering the agents to experimental animals and comparing the results with those obtained with known anorexigenic agents.

Anorexia Test Procedure

Female CF$_1$ mice, which had been fasted for 17 to 21 hours, were dosed orally with the test compound (ten or more mice per dose). One-half hour later, each mouse was transferred to an individual compartment (13.3 cm × 12.7 cm × 12.7 cm) with a 0.64 cm × 0.64 cm wire mesh floor. Inside each compartment was a brass bar (13 cm × 1.2 cm × 1.2 cm) in the top of which were ten shallow, round spot depressions (0.8 cm diameter). Each depression contained 0.05 ml of 50% sweetened condensed milk.

Thirty minutes after the mice were transferred into the compartments, the number of milk spots each mouse had consumed was counted. Fractions of spots consumed also were estimated and counted. The percent anorexigenic effect was estimated by comparison of the mean number of spots of milk consumed per mouse at a given dose with the mean number of spots consumed per vehicle-treated control mouse. Dose-response curves were plotted and from these the ED50%, the dose at which treated mice would be expected to consume 50% as much milk as control mice, was calculated.

In Table I, the oral ED50% values of nalbuphine hydrochloride, nalmetrene, and nalmetrene hydrochloride are compared with those for other anorexigenic agents.

TABLE I

|  | ED50% (mg/kg) | N* |
|---|---|---|
| Nalbuphine HCl | 71. | 40 |
| Nalmetrene | 6.7 | 20 |
| Nalmetrene HCl | 3.4 | 20 |
| Naloxone HCl | 23. | 20 |
| Naltrexone HCl | 3.0 | 20 |
| Amphetamine HCl | 0.91 | 80 |
| Fenfluramine HCl | 13.5 | 20 |

*N = number of mice in test

Since nalbuphine and nalmetrene cause decreased food intake in mice, it is expected that they will be suitable for the treatment of obesity in humans.

The active ingredient can be administered orally in solid dosage forms, such as capsules, tablets, and powders, or in liquid dosage forms, such as elixirs, syrups, and suspensions.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The dose which would constitute an anorexigenically effective dose in a given mammal would be readily determined by one skilled in the art. Based upon the data set forth in the table, the human oral dose of nalmetrene for use as an anorectic is, according to this invention, about 20 to 200 mg per day, preferably 40 mg given 3 or 4 times daily or 120–160 mg total daily dose.

Similarly, nalbuphine hydrochloride would be used as an anorectic in humans at an oral dose of about 200 to 2000 mg per day, preferably 400 mg given 3 or 4 times daily or 1200–1600 mg total daily dose.

The following provides an example of a suitable dosage form. Equivalent materials and techniques may be used also.

| | |
|---|---|
| Nalmetrene HCl | 40 mg/tablet |
| Lactose, U.S.P. | 230 mg/tablet |
| Microcrystalline Cellulose, N.F. | 23 mg/tablet |
| Stearic acid | 7 mg/tablet |

Nalmetrene HCl, lactose and microcrystalline cellulose are passed through a fine mesh screen and blended thoroughly. Stearic acid is then added to the mixture which is blended until homogeneous. The blended mixture is compressed into tablets weighing 300 mg each.

What is claimed is:

1. A method for exerting an anorexigenic effect in a mammal which comprises orally administering to said mammal an effective anorexigenic amount of nalmetrene or a pharmaceutically suitable salt thereof.

2. The method of claim 1 wherein nalmetrene is orally administered to a mammal.

3. The method of claim 1 wherein said mammal is a human being.

4. The method of claim 2 wherein said mammal is a human being.

* * * * *